United States Patent
Polsinelli et al.

(10) Patent No.: US 7,307,265 B2
(45) Date of Patent: Dec. 11, 2007

(54) THREE SECTION PIG FOR RADIO-PHARMACEUTICALS

(75) Inventors: Perry Polsinelli, Suwanee, GA (US); Jeff D. D'Alonzo, Dacula, GA (US); Steven B. West, Ball Ground, GA (US)

(73) Assignee: United Pharmacy Partners, Inc., Suwanee, GA (US)

( * ) Notice: Subject to any disclaimer, the term of this patent is extended or adjusted under 35 U.S.C. 154(b) by 238 days.

(21) Appl. No.: 11/234,403

(22) Filed: Sep. 23, 2005

(65) Prior Publication Data

US 2006/0293553 A1 Dec. 28, 2006

Related U.S. Application Data

(63) Continuation-in-part of application No. 11/168,813, filed on Jun. 28, 2005.

(51) Int. Cl.
*G21F 5/00* (2006.01)
(52) U.S. Cl. .................. 250/507.1; 250/506.1
(58) Field of Classification Search ............. 250/506.1, 250/507.1
See application file for complete search history.

(56) References Cited

U.S. PATENT DOCUMENTS

| | | | |
|---|---|---|---|
| 5,828,073 A | 10/1998 | Zhu et al. | |
| 5,927,351 A | 7/1999 | Zhu et al. | |
| 6,425,174 B1 | 7/2002 | Reich | |
| 6,576,918 B1 | 6/2003 | Fu et al. | |
| 6,586,758 B2 | 7/2003 | Martin | |
| 6,614,040 B1 * | 9/2003 | Zens | 250/515.1 |
| 6,722,499 B2 | 4/2004 | Reich | |
| 6,822,253 B1 | 11/2004 | Martin et al. | |
| 2002/0115980 A1 | 8/2002 | Niedospial, Jr. et al. | |
| 2002/0195575 A1 | 12/2002 | Martin | |
| 2003/0226981 A1 | 12/2003 | Schmidt | |

\* cited by examiner

*Primary Examiner*—David Vanore
(74) *Attorney, Agent, or Firm*—Bryan W. Bockhop; Bockhop & Associates, LLC

(57) ABSTRACT

A radio-pharmaceutical pig for transporting a syringe containing a radio-pharmaceutical includes a first cylindrical member having a first tungsten body defining a first cavity therein. A second cylindrical member has a second tungsten body defining a second cavity therethrough and is capable of engagement with the first cylindrical member so that the first cavity is in substantial alignment with the second cavity. A third cylindrical member includes a third tungsten body defining a third cavity and is capable of engagement with the second cylindrical member so that the third cavity is in substantial alignment with the second cavity. The first cavity, the second cavity and the third cavity are shaped so as to be complimentary in shape of the syringe.

10 Claims, 4 Drawing Sheets

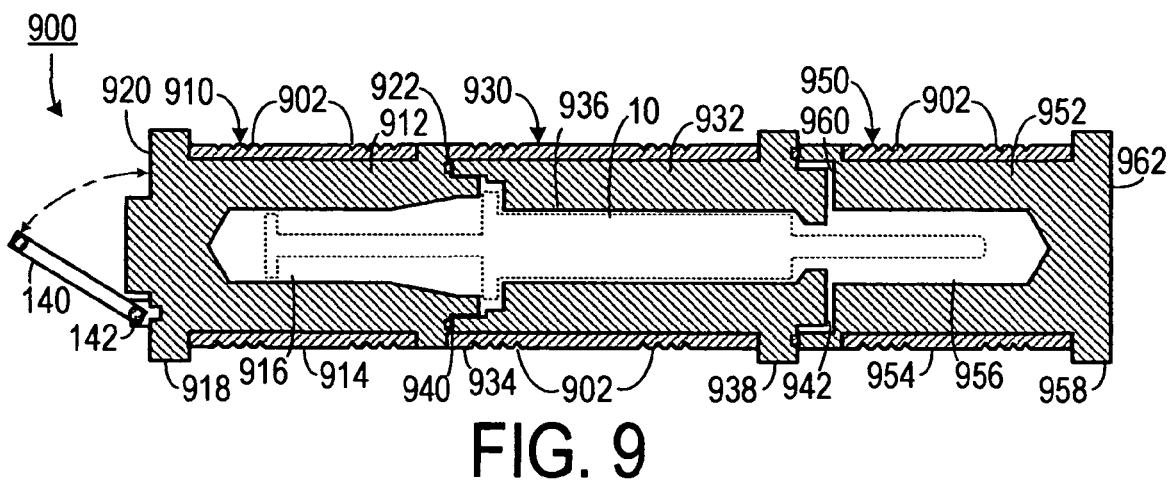
FIG. 9
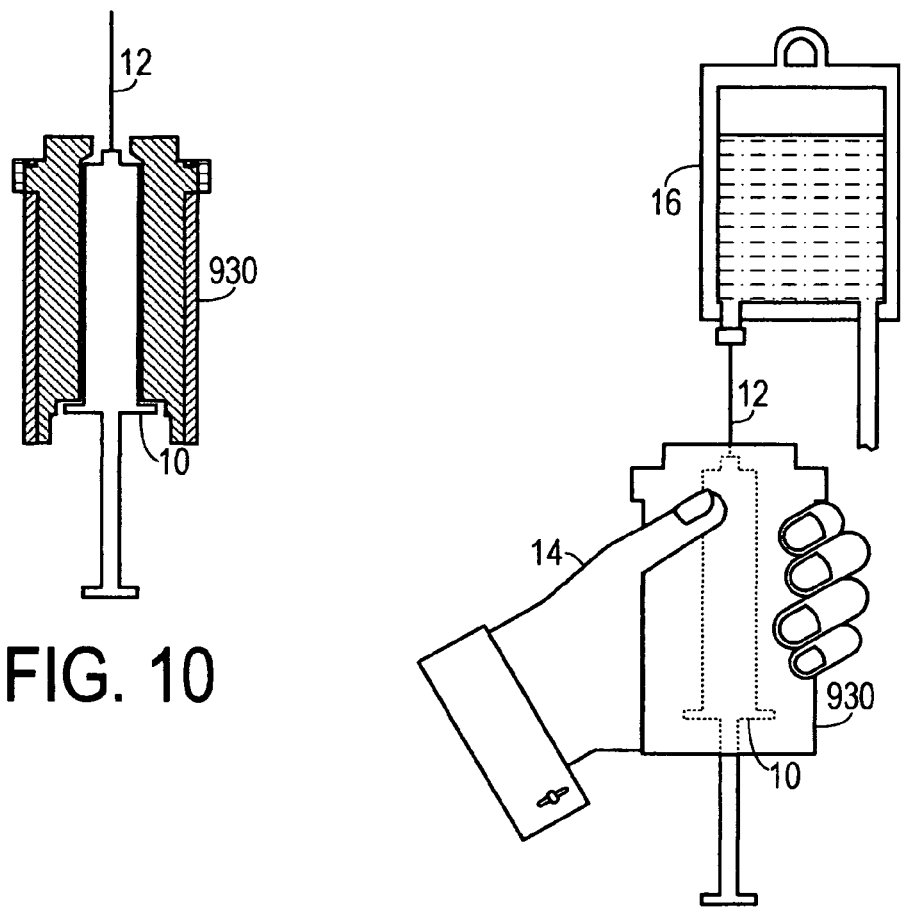
FIG. 10
FIG. 11

THREE SECTION PIG FOR RADIO-PHARMACEUTICALS

CROSS-REFERENCE TO RELATED APPLICATION AND PRIORITY CLAIM

This application is a continuation-in-part of, and claims the benefit of, U.S. patent application Ser. No. 11/168,813, filed Jun. 28, 2005, the entirety of which is hereby incorporated herein by reference.

BACKGROUND OF THE INVENTION

1. Field of the Invention

The present invention relates to medical devices and, more specifically, to a device for transporting radio-pharmaceuticals used in positron emission tomography.

2. Description of the Prior Art

Positron emission tomography (PET) imaging is a diagnostic examination that involves acquiring physiologic images based on the detection of positron radiation. Positrons are particles emitted from radioactive substances. The radioactive substances used are injected into a patient and positrons from the radioactive substance are detected and imaged by a PET scanner. The resulting images are used to evaluate a variety of diseases.

Pharmaceutical compositions used in PET scans are administered in liquid form by injection into the patient. Radio-pharmacists typically calculate a unit dose based on the amount of decay that a dose will undergo during transport to the hospital at which the dose will be administered. In preparing the dose, the radio-pharmacist places the dose into a syringe and then places the syringe into a "pig" that shields those handling the dose from the radioactive contents of the syringe. The pig is then transported to the hospital for administration to a patient.

With many types of radio-pharmaceuticals, a lead pig is sufficient to shield those handling the dose. However, for radio-pharmaceuticals designed for PET scans, a typical lead-shielded pig does not provide sufficient protection by itself To compensate, existing PET radio-pharmaceutical transport systems require an extra level of shielding. This is accomplished by providing a secondary shielded case for the pig. Such a shielded case includes lead shielding about a cylindrical opening into which the pig fits.

Existing PET radio-pharmaceutical pigs tend to need to be replaced on a regular basis. This is because the shielding quality of lead breaks down in the presence of PET pharmaceutical radiation. Thus, the cost is increased. Also, there is a danger of insufficient protection if a radio-pharmacist continues to use a pig past its designed life span.

Because most pigs are roughly cylindrical in shape, rolling of such pigs is a problem If a pig is allowed to roll, it could roll off of the surface on which it is placed and fall, causing injury, destroying the dose of the radio-pharmaceutical composition contained therein, or both. Some existing pigs include a flat surface milled into the outer surface of the pig. The milling is done by removing several exterior chords of the cylinder forming the pig, thereby forming flat surfaces. Also, several small evenly-spaced bumps may be added to the exterior surface of the pig. Both of these methods of preventing rolling may be satisfactory for ordinary conditions, but they do not provide a sufficient anti-roll capability in situations in which a pig is accidentally bumped with considerable force. Furthermore, most pigs include two sections that must be separated when accessing the syringe inside. However, many existing pigs usually include anti-roll texturing on only one section. Thus, if the section without the anti-roll texturing is placed on a table, it may roll off and cause injury.

Typical radio-pharmaceutical pigs have an inner chamber into which a filled syringe is placed. A plastic liner is frequently employed to prevent spillage from the syringe from accumulating inside the pig. Such a liner is typically made from rigid plastic and used only once. Because the liner is rigid, it takes up a considerable amount of space to store and to dispose of.

Typically, when administering a radio-pharmaceutical to a patient, the syringe is removed from the pig and placed in a shielded holder that protects the physician's hands from radiation while injecting the radio-pharmaceutical into an IV bag. The transfer of the syringe causes a brief exposure to the user and increases the risk that the syringe could fall and be harmed.

Therefore, it would be desirable for a radio-pharmaceutical pig to be capable of providing a mechanism for administering a radio-pharmaceutical without having to transfer it to a shielded holder.

SUMMARY OF THE INVENTION

The disadvantages of the prior art are overcome by the present invention which, in one aspect, is a radio-pharmaceutical pig for transporting a syringe containing a radio-pharmaceutical. A first cylindrical member includes a first tungsten body defining a first cavity therein opening to a first end. A second cylindrical member includes a second tungsten body defining a second cavity therethrough and includes a proximal end and an opposite distal end. The proximal end is capable of engagement with the first end of the first cylindrical member so that the first cavity is in substantial alignment with the second cavity. An anti-roll structure extends outwardly from a portion of the second cylindrical member. The second cylindrical member also includes an external stainless steel sleeve covering a portion of the second cylindrical member. The stainless steel sleeve includes a gripping surface cut into the second external stainless steel sleeve. A third cylindrical member includes a third tungsten body defining a third cavity opening to a primary end. The primary end is capable of engagement with the distal end of the second cylindrical member so that the third cavity is in substantial alignment with the second cavity, wherein the first cavity, the second cavity and the third cavity are shaped so as to be complimentary in shape of the syringe.

In another aspect, the invention is a method for using a three section pig. The pig includes a first member, a second member and a third member. A radio-pharmaceutical filled syringe, having a needle extending therefrom, is placed in the pig. The second member is disengaged from the first member and the third member. The second member is gripped with the syringe disposed in the second member so that the needle extends from one end of the second member. At least a portion of the radio-pharmaceutical is injected into a receptacle.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

BRIEF DESCRIPTION OF THE FIGURES OF THE DRAWINGS

FIG. 9 is a cross sectional view of a three section pig.

FIG. 10 is a cross sectional view of the center section of a three section pig as it is ready for administration of a radio-pharmaceutical.

FIG. 11 is a plan view of the center section shown in FIG. 10 being employed.

DETAILED DESCRIPTION OF THE INVENTION

Figure 1:
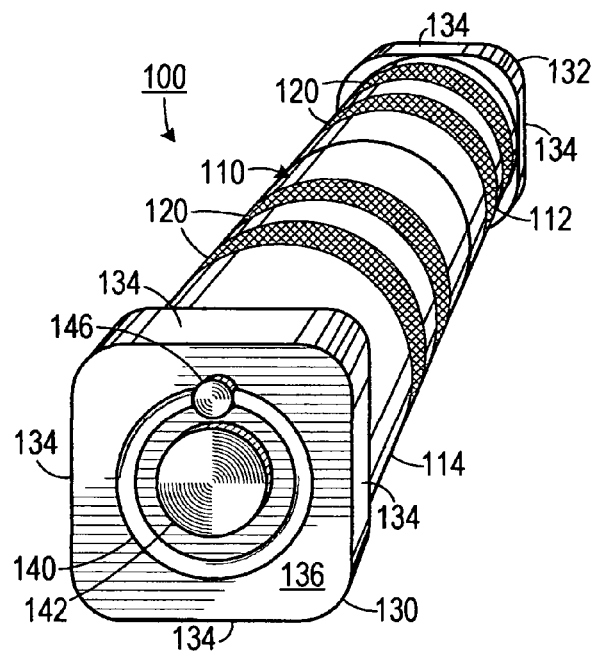
FIG. 1 is a top perspective view of one illustrative embodiment of the invention.

A preferred embodiment of the invention is now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on."

As used herein, "plastic" means capable of being deformed without rupture and a "plastic material" includes materials that are deformable. Plastic materials, as used herein, include, but are not limited to, synthetic polymer materials, natural latex materials, thin metal sheets and combinations thereof It will be readily understood that many other materials, not specifically listed herein, will meet the criteria for being a plastic within the scope of the present invention.

As shown in FIG. 1, one illustrative embodiment of a radio-pharmaceutical pig 100 includes a tungsten cylinder 110 having a first elongated member 112 and a second elongated member 114. The outer surface of the first elongated member 112 and the second elongated member 114 includes a rough textured portion 120 that facilitates gripping of the pig 100 by a user. Typically, the pig 100 is formed from titanium stock and formed on a metal lathe using conventional methods.

Figure 2A:
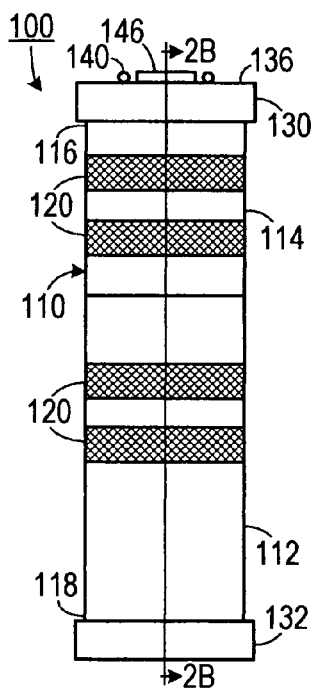
FIG. 2A is an elevational view of one embodiment.
Figure 2B:
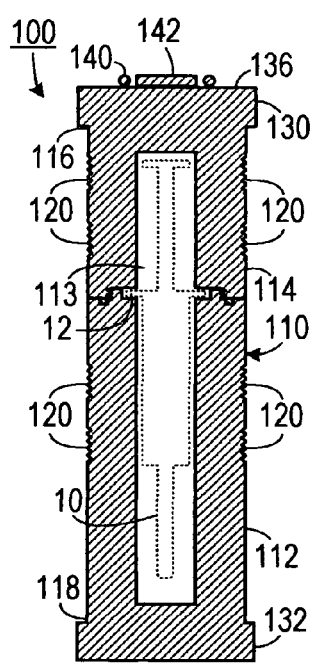
FIG. 2B is a cross-sectional view of the embodiment shown in FIG. 2A, taken along line 2B-2B.
Figure 2C:
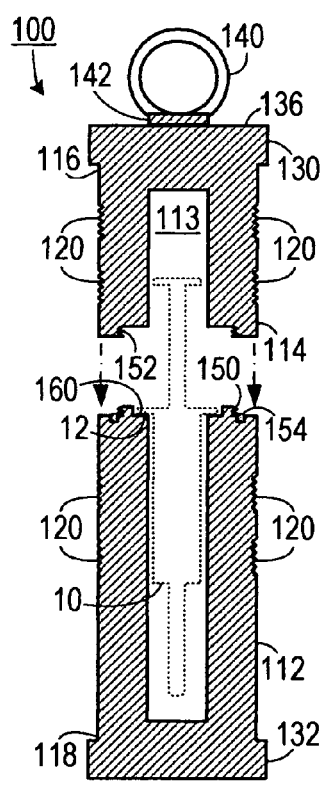
FIG. 2C is an expanded cross-sectional view of the embodiment shown in FIG. 2B.

As shown in FIGS. 2A-2C, the first elongated member 112 terminates in a first engagement surface 150 and an opposite first distal end 118, the second elongated member 114 terminating in a second engagement surface 152 that is complimentary to the first engagement surface 150 and an opposite second distal end 116. The pig 100 defines an elongated cavity 113 therein that is substantially coaxial with the tungsten cylinder 110. The cavity 113 is of sufficient size to receive a syringe 10 therein. The tungsten cylinder 110 is thick enough to shield users from a PET radio-pharmaceutical without requiring additional shielding. The actual thickness may be calculated easily by referring to standard radiological shielding tables and depends on the type and amount of radio-pharmaceutical being used.

A recess 160 may be milled into either the first engagement surface 150 or the second engagement surface 152 (or both) to receive the finger grip tabs of the syringe 10, thereby preventing the syringe 10 from rocking during transport An O-ring 154 may be embedded in one of the engagement surfaces 150 or 152 to prevent leakage from the pig 100.

Returning to FIG. 1, a first anti-roll member 132 extends outwardly from the first distal end 118 and a second anti-roll member 130 extends outwardly from the second distal end 116. The first anti-roll member 132 and the second anti-roll member 130 each include at least three (and in the embodiment shown, four) flat surfaces 134 that inhibit rolling. Including an anti-roll member 132 and 130 on each of the first elongated member 112 and the second elongated member 114, ensures that neither member will roll if left unattended on a flat surface. This may be a substantial advantage, given that each elongated member 112 and 114 will likely be quite heavy due to the thickness of the tungsten employed.

Figure 2D:
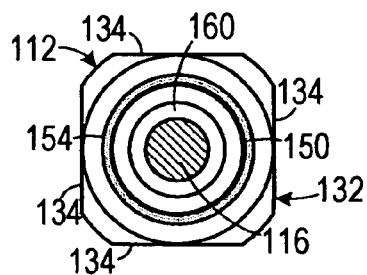
FIG. 2D is a bottom plan view of the embodiment shown in FIG. 2A.
Figure 2E:
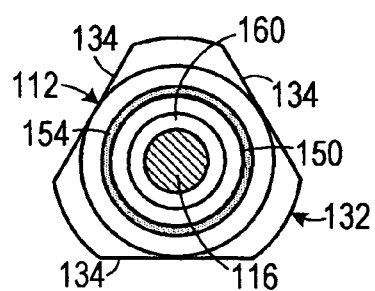
FIG. 2E is a bottom plan view of an alternate embodiment of the invention

The second distal end 116 is supplied with a lifting ring 140 that facilitates lifting of the pig 100 out of any carrying container (not shown) used to transport the pig 100. The lifting ring may be affixed to the top surface 136 of the pig 100 with an attachment 146 and a spacing plug 142 may be affixed to the top surface 136 inside the ring 140 when the ring 140 is in the down position As shown in FIG. 2D, the anti-roll members 132 are blocks of titanium that could include four flat sides 134, or, as shown in FIG. 2E, only three flat sides 134, or even more than four flat sides 134, so long as the flat side 134 has dimensions sufficient to prevent rolling. The anti-roll members 132 may be formed from the same titanium stock as the rest of the pig 100.

Figure 2F:
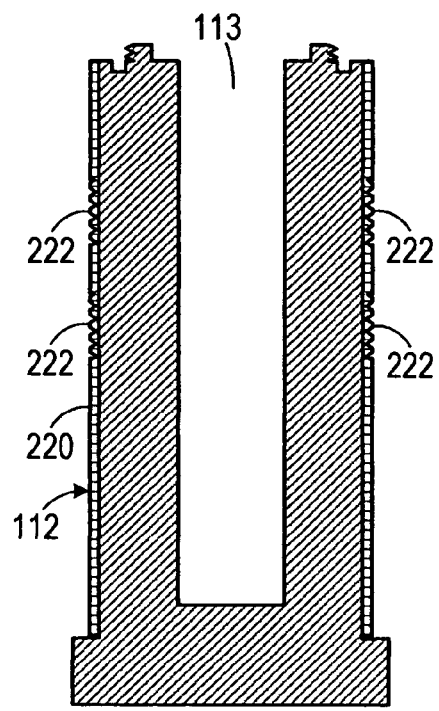
FIG. 2F is a cross sectional view of a detail of the embodiment shown in FIG. 2B.

As shown in FIG. 2F, a stainless steel sleeve 220 may disposed about a portion of the tungsten cylinder 110. The textured portion 222 may be cut into the stainless steel sleeve 220 and may include diamond patterned scoring.

Figure 3:
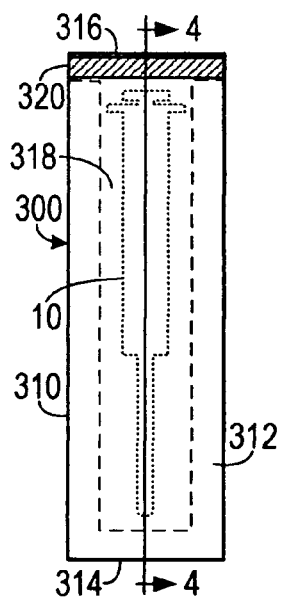
FIG. 3 is a plan view of a plastic insert.
Figure 4A:
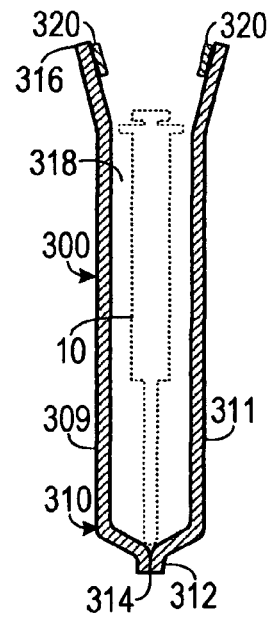
FIG. 4A is a cross-sectional view of the insert shown in FIG. 3, taken along line 4-4.
Figure 4B:
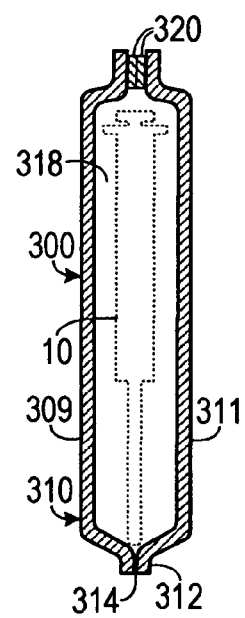
FIG. 4B is a second cross-sectional view of the insert shown in FIG. 3, taken along line 4-4.
Figure 5:
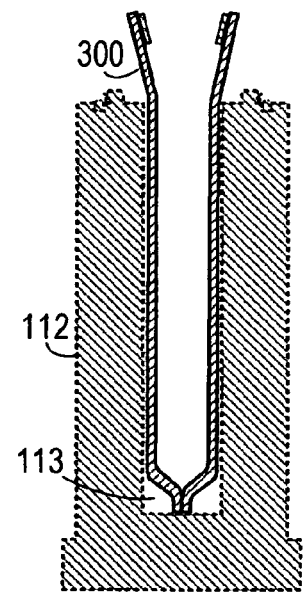
FIG. 5 is a cross-sectional view of an insert disposed within a pig.

As shown in FIGS. 3-5, a disposable plastic insert 300 is disposed within the cavity 113 to prevent leakage of radio-pharmaceutical materials into the cavity 113. Each insert 300 includes an elongated plastic envelope 310 made from a first plastic sheet 309 and an oppositely-disposed second plastic sheet 311 that are sealed together along a sealing surface 312 (through thermal sealing, for example) and that open to a top side 316, thereby defining passage therein 318. The passage is of sufficient size to allow a syringe 10 to fit therein. The disposable plastic insert 300 could be made of materials including polyethylene and polyvinyl chloride, but should be thick enough to resist punctures from any exposed needles placed into the insert 300.

A first adhesive tab 320 is placed on the first sheet 309 adjacent the top side 316 and a second adhesive tab 320 is placed on the second sheet 311 adjacent the top side 316. The first adhesive tab 320 and the second adhesive tab 320 each include a peel-off cover that may be peeled off to allow exposure of the adhesive tabs 320 so as to facilitate sealing the top side (as shown in FIG. 4B). This facilitates easy sealing of the syringe 10 for disposal after use.

Figure 6:
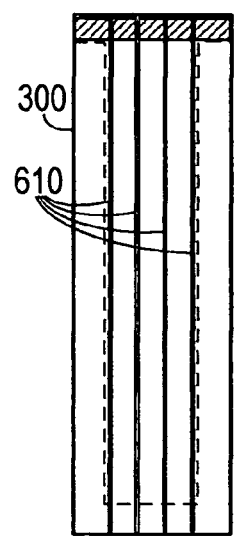
FIG. 6 is a plan view of a plastic insert including stiffening ribs.

As shown in FIG. 6, the disposable plastic insert 300 may also include a plurality of elongated rib structures 610 embedded in one of the plastic sheets 310 and 311 to provide structural support to the plastic insert 300. The elongated ridge structures 610 could include wires embedded in one of the plastic sheets 310 and 311, or could be thickened plastic that is molded into the plastic sheets 310 and 311 using commonly-known plastic sheet forming methods.

Figure 7:
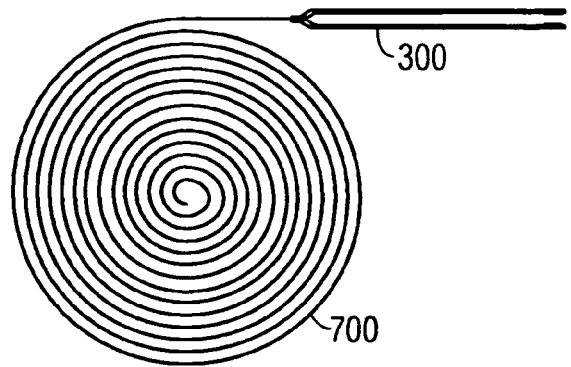
FIG. 7 is a side view of a roll of plastic inserts.
Figure 8:
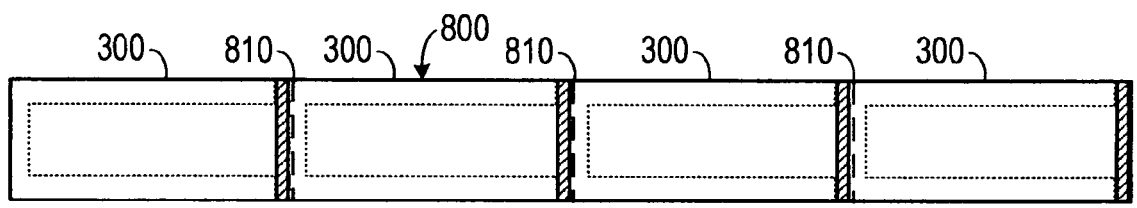
FIG. 8 is a plan view of a strip of plastic inserts.

As shown in FIG. 7, because the inserts 300 are flexible, a plurality of inserts 300 may be formed continuously and stored in the form of a roll 700. This facilitates easy manufacturing and storage of the inserts. As shown in FIG. 8, when the inserts are formed as a continuous strip 800, a serration 810 may be cut in the sealed portion between each successive insert 300 in the strip 800 to facilitate separation of the inserts 300.

A three section embodiment is shown in FIGS. 9-11. As shown in FIG. 9, the radio-pharmaceutical pig 900 includes a first cylindrical member 910, a second cylindrical member 930 and a third cylindrical member 950. The first cylindrical member 910 includes a first tungsten body 912 defining a first cavity 916 that opens to a first end 922. A first anti-roll structure 918 extends outwardly from a second end 920. The first cylindrical member 910 also includes a first external stainless steel sleeve 914 that covers a portion of the first cylindrical member 910. Cut into the first external stainless steel sleeve 914 is a gripping surface 902, which could be a diamond pattern scored surface.

The second cylindrical member 930 includes a second tungsten body 932 that defines a second cavity 936 therethrough. The second cylindrical member 930 includes a proximal end 940 and an opposite distal end 942. The proximal end 940 is capable of engaging (such as with complimentary threading, etc.) the first end 922 of the first cylindrical member 910 so that the first cavity 916 is in substantial alignment with the second cavity 936. A second anti-roll structure 938 extends outwardly from a portion of the second cylindrical member 930. As demonstrated in FIG. 11, the second anti-roll structure 938 also prevents slippage of the second cylindrical member 930 when it is being used to shield the user during delivery of the radio-pharmaceutical. Returning to FIG. 9, the second cylindrical member 930 also includes a second external stainless steel sleeve 934 that covers a portion of the second cylindrical member 930, with a gripping surface 902 cut into the second external stainless steel sleeve 934.

The third cylindrical member 950 includes a third tungsten body 952 that defines a third cavity 956 that opens to a primary end 960. The primary end 960 is capable of engaging the distal end 942 of the second cylindrical member 930 so that the third cavity 956 is in substantial alignment with the second cavity 936. A third anti-roll structure 958 extends outwardly from a secondary end 962 of the third cylindrical member 950. The third cylindrical member 950 also includes a third external stainless steel sleeve 954 that covers a portion of the third cylindrical member 950 with a gripping surface 902 cut into the third external stainless steel sleeve 954. The first cavity 916, the second cavity 936 and the third cavity 956 are shaped so as to be complimentary in shape of the syringe 10.

As shown in FIG. 10, the second cylinder member 930 may be disengaged from the first cylinder member 910 and the third cylinder member 950. The second cylinder member 930 has dimensions that allow it to be used to shield the syringe 10 while the syringe 10 is being used to deliver the radio-pharmaceutical to a receptacle. This is shown in FIG. 11, wherein the physician 14 grips the second cylinder member 930 with the syringe 10 disposed therein. The needle 12 extends from the second cylinder member 930 so that the physician 14 can inject the contents of the syringe 10 into a receptacle 16 (such as an injection port of an IV bag).

The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. A radio-pharmaceutical pig, for transporting a syringe containing a radio-pharmaceutical, comprising:
   a. a first cylindrical member, including a first tungsten body defining a first cavity therein opening to a first end;
   b. a second cylindrical member, including a second tungsten body defining a second cavity therethrough, including a proximal end and an opposite distal end, the proximal end capable of engagement with the first end of the first cylindrical member so that the first cavity is in substantial alignment with the second cavity, an anti-roll structure extending outwardly from a portion of the second cylindrical member, the second cylindrical member also including an external stainless steel sleeve covering a portion of the second cylindrical member with a gripping surface cut into the second external stainless steel sleeve;
   c. a third cylindrical member, including a third tungsten body defining a third cavity opening to a primary end, the primary end capable of engagement with the distal end of the second cylindrical member so that the third cavity is in substantial alignment with the second cavity,
   wherein the first cavity, the second cavity and the third cavity are shaped so as to be complimentary in shape of the syringe.

2. The radio-pharmaceutical transport system of claim 1, wherein the second cylinder member may be disengaged from the first cylinder member and the third cylinder member and wherein the second cylinder member has dimensions that allow the second cylinder member to be used to shield the syringe while the syringe is being used to deliver the radio-pharmaceutical to a receptacle.

3. The radio-pharmaceutical transport system of claim 1, wherein the gripping surface comprises a diamond patterned scoring.

4. The radio-pharmaceutical transport system of claim 1, wherein the first anti-roll member and the second anti-roll member each comprise a block that extends outwardly from the tungsten cylinder, the block having at least three substantially flat sides.

5. The radio-pharmaceutical transport system of claim 4, wherein the block has four substantially flat sides.

6. A radio-pharmaceutical pig, for transporting a syringe containing a radio-pharmaceutical, comprising:
   a. a first cylindrical member, including a first tungsten body defining a first cavity therein opening to a first end, a first anti-roll structure extending outwardly from a portion of the first cylindrical member, the first cylindrical member also including a first external stainless steel sleeve covering a portion of the first cylindrical member with a gripping surface cut into the first external stainless steel sleeve;
b. a second cylindrical member, including a second tungsten body defining a second cavity therethrough, including a proximal end and an opposite distal end, the proximal end capable of engagement with the first end of the first cylindrical member so that the first cavity is in substantial alignment with the second cavity, a second anti-roll structure extending outwardly from a portion of the second cylindrical member, the second cylindrical member also including a second external stainless steel sleeve covering a portion of the second cylindrical member with a gripping surface cut into the second external stainless steel sleeve;
c. a third cylindrical member, including a third tungsten body defining a third cavity opening to a primary end, the primary end capable of engagement with the distal end of the second cylindrical member so that the third cavity is in substantial alignment with the second cavity, a third anti-roll structure extending outwardly from a portion of the third cylindrical member, the third cylindrical member also including a third external stainless steel sleeve covering a portion of the third cylindrical member with a gripping surface cut into the third external stainless steel sleeve, wherein the first cavity, the second cavity and the third cavity are shaped so as to be complimentary in shape of the syringe.

7. The radio-pharmaceutical transport system of claim 6, wherein the second cylinder member may be disengaged from the first cylinder member and the third cylinder member and wherein the second cylinder member has dimensions that allow the second cylinder member to be used to shield the syringe while the syringe is being used to deliver the radio-pharmaceutical to a receptacle.

8. The radio-pharmaceutical transport system of claim 6, wherein the gripping surface comprises a diamond patterned scoring.

9. The radio-pharmaceutical transport system of claim 6, wherein the first anti-roll member and the second anti-roll member each comprise a block that extends outwardly from the tungsten cylinder, the block having at least three substantially flat sides.

10. The radio-pharmaceutical transport system of claim 6, wherein the block has four substantially flat sides.

* * * * *